(12) United States Patent
Hurst

(10) Patent No.: US 6,936,048 B2
(45) Date of Patent: Aug. 30, 2005

(54) ECHOGENIC NEEDLE FOR TRANSVAGINAL ULTRASOUND DIRECTED REDUCTION OF UTERINE FIBROIDS AND AN ASSOCIATED METHOD

(75) Inventor: Bradley Shawn Hurst, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 183 days.

(21) Appl. No.: 10/345,635

(22) Filed: Jan. 16, 2003

(65) Prior Publication Data

US 2004/0143252 A1 Jul. 22, 2004

(51) Int. Cl.[7] ............................................. A61B 18/18
(52) U.S. Cl. ...................... 606/41; 600/439; 600/461
(58) Field of Search ........................ 606/41, 42, 45–50; 600/439, 459, 461–464

(56) References Cited

U.S. PATENT DOCUMENTS

| | | | |
|---|---|---|---|
| 1,562,460 A | | 11/1925 | McFee |
| 4,883,059 A | | 11/1989 | Stedman et al. |
| 5,501,681 A | | 3/1996 | Neuwirth et al. |
| 5,662,680 A | * | 9/1997 | Desai .......................... 606/210 |
| 5,921,933 A | * | 7/1999 | Sarkis et al. ................. 600/459 |
| 5,979,453 A | * | 11/1999 | Savage et al. ............... 128/898 |
| 6,032,673 A | | 3/2000 | Savage et al. |
| 6,039,748 A | | 3/2000 | Savage et al. |
| 6,095,981 A | * | 8/2000 | McGahan .................... 600/461 |
| 6,113,594 A | | 9/2000 | Savage |
| 6,146,378 A | | 11/2000 | Mikus et al. |
| 6,190,386 B1 | | 2/2001 | Rydell |
| 6,231,591 B1 | | 5/2001 | Desai |
| 6,280,441 B1 | | 8/2001 | Ryan |
| 6,379,348 B1 | | 4/2002 | Onik |
| 6,461,296 B1 | | 10/2002 | Desai |
| 6,770,070 B1 | * | 8/2004 | Balbierz ....................... 606/41 |
| 2002/0198518 A1 | | 12/2002 | Mikus et al. |

FOREIGN PATENT DOCUMENTS

| | | |
|---|---|---|
| DE | 197 13 797 A1 | 10/1997 |
| WO | WO 97/17105 | 5/1997 |

OTHER PUBLICATIONS

PCT Written Opinion of the International Searching Authority for PCT/US2004/000773.

* cited by examiner

*Primary Examiner*—Michael Peffley
(74) *Attorney, Agent, or Firm*—Alston & Bird LLP

(57) ABSTRACT

The invention is a transvaginal ultrasound probe having an attached echogenic needle that is useful in the treatment of uterine fibroids. The echogenic needle has an echogenic surface near its tip that allows the physician to visualize its location using ultrasound imaging. In one embodiment, the needle has an active electrode at its distal end. The active electrode supplies radio frequency energy to a fibroids causing necrosis of the targeted fibroid or by destroying the fibroid's vascular supply. The radio frequency needle preferably has a safety device that shuts-off energy if the needle punctures the uterine wall. In a second embodiment, the needle has a cryogen supply tube and cryogen supply. This embodiment destroys fibroid tissue by freezing it or its vascular supply when the tissue comes in contact with the needle's frozen distal end. The invention further includes the method of using the ultrasound probe with the attached needle.

26 Claims, 5 Drawing Sheets

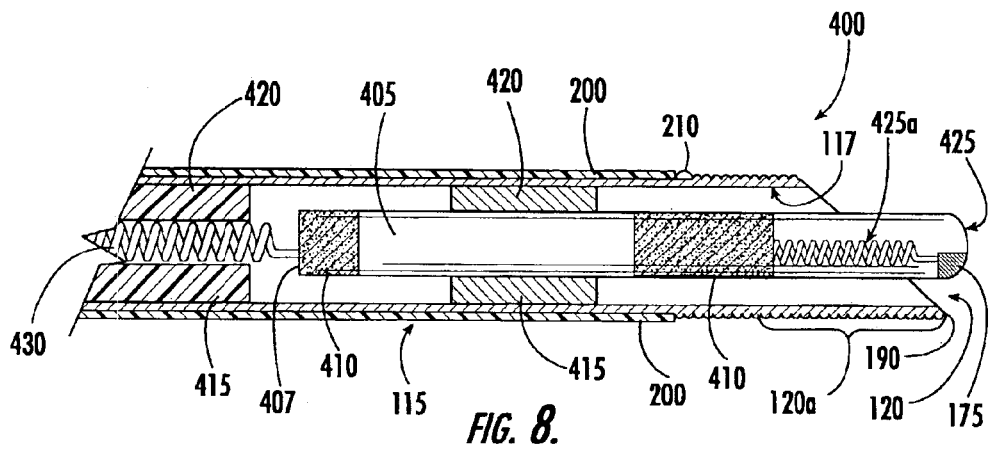
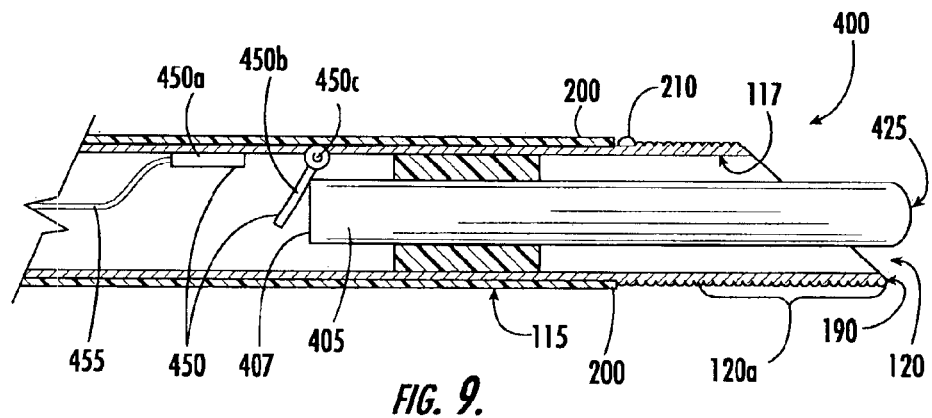
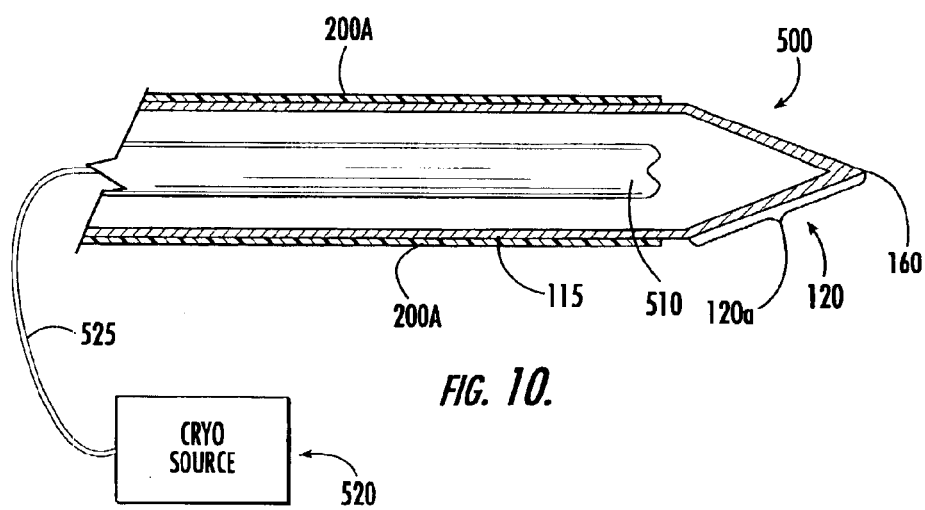

ECHOGENIC NEEDLE FOR TRANSVAGINAL ULTRASOUND DIRECTED REDUCTION OF UTERINE FIBROIDS AND AN ASSOCIATED METHOD

BACKGROUND OF THE INVENTION

This invention relates to surgical needles for tissue ablation, and more particularly, to surgical needles that are for ablation of uterine fibroids.

Approximately 20 to 40 percent of women have uterine fibroids (licomyomata). In the United States, fibroids result in approximately 175,000 hysterectomies and 20,000 myomectomies each year. Fibroids are well-defined, non-cancerous tumors that arise from the smooth muscle layer of the uterus. Approximately 25% of women suffer fibroid related symptoms, including menorrhagia (prolonged or heavy menstrual bleeding), pelvic pressure or pain, and reproductive dysfunction.

The most common treatments for fibroids include hysterectomy, abdominal myomectomy, laparoscopic myomectomy, hysteroscopic myomectomy, laparoscopy-directed needle mylosis, laparoscopy-directed needle cryomyolysis, high-intensity focused ultrasound ablation of fibroids, and uterine artery embolization. Hysterectomy is a major surgical procedure and carries with it the usual risk of surgery, such as hemorrhaging, lesions, complications, pain, and prolonged recovery. The majority of myomectomies are performed abdominally, wherein a surgeon creates an abdominal incision through which individual fibroids are removed. Abdominal myomectomy and laparoscopic myomectomy, like a hysterectomy, carries the usual risk of surgery.

Radio Frequency (RF) myolysis and thermal tissue ablation are two promising methods for treating fibroids. RF myolysis is a technique in which a RF probe is inserted into a fibroid or the surrounding tissue and then RF energy is applied to the tip of the probe. The tissue surrounding the tip is heated by the RF energy causing necrosis within the tissue. Thermal tissue ablation is a technique that is performed with a cryoablation probe. The cryoablation probe destroys the fibroid tissue by freezing it.

Current methods incorporating RF or cryoablation techniques require direct visualization of the needle tip or electronic imaging. Normally, under direct visualization techniques an endoscope is inserted into the uterus to position the needle. Direct visualization is often problematic because of the difficulties involved in simultaneously manipulating the endoscope and needle. Typically, when electronic imaging is used, the position of the needle is visualized with a hysteroscope or with an external abdominal ultrasound. Hysteroscopy allows direct visualization of the uterine cavity by inserting a small camera on the end of a long tube directly into the uterus through the vagina and cervix. Similar to an endoscope, a hysteroscope must be simultaneously manipulated with the needle, and thus is problematic. Monitoring the probe's position with current ultrasound techniques has a number of drawbacks. For example, a clinician using ultrasound imaging from an external source will have difficulty in distinguishing the uterine tissue from the surrounding organs and precisely locating the needle.

U.S. Pat. No. 5,979,453 to Savage et al. describes a myolysis needle that requires laparoscopic surgery. In laparoscopic surgery the needle must be placed through the uterine serosa into or near the fibroid. As a result, uterine adhesions often form that may cause chronic pain, infertility, and bowel obstruction. Additionally, during laparoscopic surgery the surgeon cannot visualize the tissue below the surface and must blindly place the needle, as a result placement may be sub-optimal.

U.S. Pat. No. 6,146,378 to Mikus et al. discloses a needle placement guide having an endoscope that is inserted into the uterus through the vagina. Using the endoscope, the surgeon positions the endoscopic guide in the correct orientation to the targeted fibroid. After positioning the guide, the endoscope is removed from within the guide and an ablation device is inserted into the guide for subsequent operation on the fibroid. The needle guide suffers from several disadvantages. There is the risk that the needle guide could shift during removal of the endoscope and insertion of the ablation device, resulting in sub-optimal performance. The needle cannot be relocated during the ablation procedure and the endoscope must be reinserted whenever it is necessary to reposition the needle guide. Reinserting and removing the endoscope and ablation device every time the needle must be repositioned increases the time and expense of the surgery.

U.S. Pat. No. 6,379,348 to Onik describes a mylolysis needle that is a combination of a cryosurgical and electrosurgical instrument for tissue ablation. The cryo/electro needle is not easily visualized when in use and requires the use of a dilator to create an access channel in the tissue area where the needle is to be inserted. Similar to laparscopic surgery, placement of the cryo/electro needle is done blindly and may not result in optimal performance.

Thus, a need exists to provide a medical needle system and method that can provide accurate and reliable targeting of fibroid tumors. It is also desirable to provide a needle that has a safety system that would shut-off electrical current to the needle if the uterine wall is punctured.

BRIEF SUMMARY OF THE INVENTION

The invention provides a medical needle for transvaginal ultrasound directed reduction of fibroids. The medical needle is adapted for use in conjunction with a transvaginal ultrasound probe. The ultrasound probe has an attached needle guide through which the needle is inserted. The needle has an outer tubular member having an inner surface, a distal end, and a proximal end. The distal end of the outer member is made of an echogenic material so that the tip of the needle has heightened visibility on an ultrasound screen. Located at the distal end is an active electrode that is in communication with a radiofrequency source. An insulating sheath surrounds the entire outer member except for a section that is near the active electrode at the distal end.

The needle has a return electrode that is optionally located on the outer member near the active electrode or on an outer tissue surface of a patient. Optionally, the needle may have a temperature sensor that is located near the active electrode. Typically, the distal end will either be a sharpened pointed tip or a beveled tip that defines an opening in the distal end.

In a preferred embodiment, the needle has a safety device that will turn off power to the active electrode if the tip of the needle should penetrate a patient's uterine wall. In the embodiment possessing a beveled tip, an inner cylindrical member having a forward end and blunt rear end is disposed within the outer member. The inner member has a cylindrical outer section that is electrically conductive and a section that is not electrically conductive. Disposed on the inner surface of the outer member is a second electrically conductive surface and a third electrically conductive surface that are not in communication with one another. The second surface is in communication with the RF power source and the third surface is in communication with active electrode.

A spring is attached to the forward end of the inner member and the blunt rear end extends outwardly beyond the beveled tip. When pressure is applied to the blunt rear end the spring is compressed and the exposed blunt rear end slides backwardly into the outer member. As the inner tubular member slides into the outer member the electrically conductive surface comes in contact with both the second and third surface so that current passes through the surfaces and RF energy is supplied to the active electrode.

In a second embodiment having a safety device, the inner tubular member does not have a conductive surface and there are no second and third conductive surfaces. Rather, a switch is located at the proximal end of the outer member. When pressure is applied to the blunt rear end of the inner member, the inner member slides back into the outer member and thereby closes the switch. When in the closed position, the switch sends a signal to the RF source and RF energy is applied to the active electrode.

In a third embodiment, the needle has an outer member, an inner surface, an echogenic distal end, and a proximal end. As in the first embodiment, the echogenic material results in the tip of the needle having a heightened visibility. Within the outer member is a cryogen tube that extends longitudinally from the proximal end to the distal end. Surrounding a section of the outer member from the proximal end to near the distal end is a cryo-insulation sheath. The distal end is in communication with a cryogen supply so that the distal end can be in cryogenic contact with fibroids.

The length of the needle in all embodiments is typically from about 25 to 50 centimeters, and somewhat more typically between 30 to 40 centimeters. The diameter of the needle in all embodiments is typically from about 12 to 18 gauge, and somewhat more typically from about 16 to 18 gauge. Normally, the needle has a handle at the proximal end that allows the user to easily grip and manipulate the needle.

The invention also includes a method for the electric surgery of fibroids using a transvaginal ultrasound directed echogenic needle. The method comprises the steps of providing a transvaginal ultrasound probe having a transducer and attached needle guide; providing an echogenic needle as described above; inserting the probe into a patient's uterus; inserting the needle into the uterus through the attached needle guide; sensing the location of the needle and fibroid using ultrasound imaging; guiding and positioning the needle on the surface of a fibroid using ultrasound imaging; and passing a controlled amount of RF energy through the fibroid. The method optionally includes the steps of monitoring tissue temperature, penetrating the surface of the fibroid with the distal end of the needle, and the step of turning off power to the active electrode if the distal end pierces the uterine wall.

The invention additionally includes the method for the cryoablation of fibroids in the uterus using a transvaginal ultrasound directed echogenic needle. The method includes the steps of providing a transvaginal ultrasound probe having a transducer and an attached needle guide; providing a cryoablation echogenic needle as described above; inserting the probe into the uterus; inserting the echogenic needle into the uterus through the attached needle guide; sensing the location of the needle and fibroid using ultrasound imaging; guiding and positioning the needle on the surface of a fibroid using ultrasound imaging; delivering a controlled amount of cryogenic supply to the distal end of the needle while it in contact with the surface of the fibroid. The method optionally includes the step of penetrating the fibroid with the distal end of the needle before or after delivering a controlled amount of cryogenic supply.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 8 is a sectional side view of a radio frequency echogenic needle having a "shut-off" mechanism and an active electrode disposed in the inner member;

FIG. 9 is a sectional side view of a radio frequency echogenic needle having a switch "shut-off" mechanism;

FIG. 10 is a sectional side view of a cryogenic ablation echogenic needle; and

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
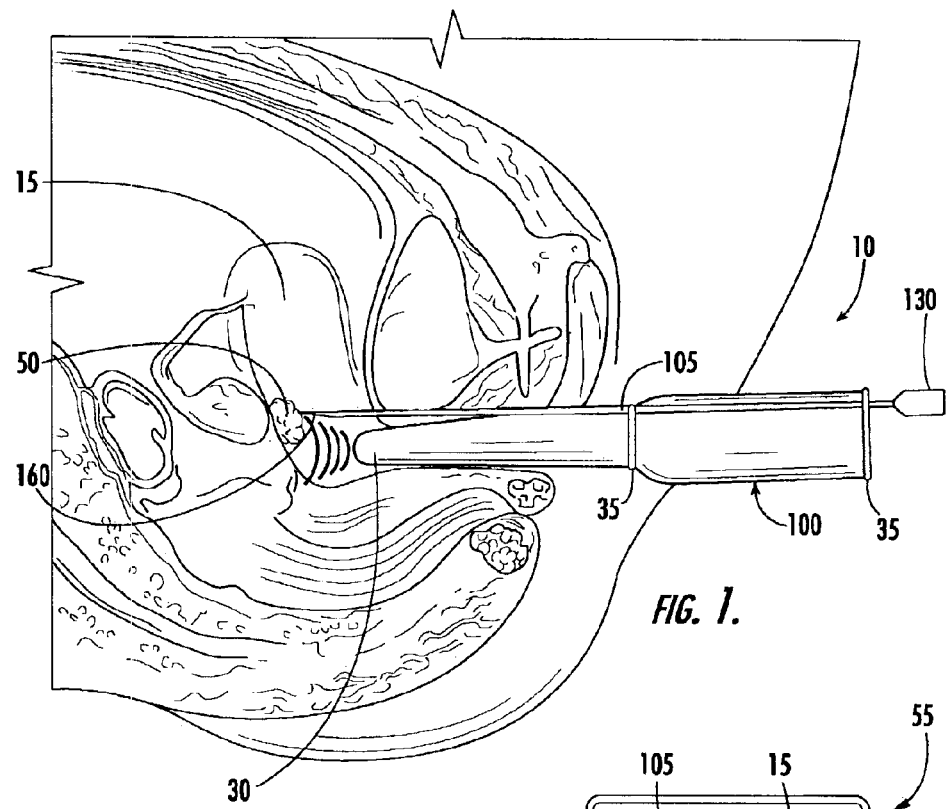
FIG. 1 is a side view of a transvaginal ultrasound probe having an attached echogenic needle that has been inserted into a uterus.

Referring more specifically to the drawings, for purposes of illustration, but not of limitation, there is shown in FIG. 1 an embodiment of the invention referred to generally as 10. FIG. 1 illustrates an ultrasound probe 100 having the attached mylosis needle 105 that is inserted into the uterus 15. The ultrasound probe has a transducer located within its tip 30 so that imaging of the uterus and needle are sent to a display for monitoring. Normally, the ultrasound probe 100 includes clamps 35 that attach the needle to the ultrasound probe. Typically, the clamps are made from a metal or plastic material that fits tightly around the probe and has an attached needle guide. The needle guide is typically a narrow or circular opening through which the needle is inserted. Alternatively, the material comprising the clamps is some other hard material that allows the user to manipulate the needle, although not necessarily with equivalent results. The ultrasound probe useful in the invention is any probe that is designed for insertion through the vagina.

Figure 2:
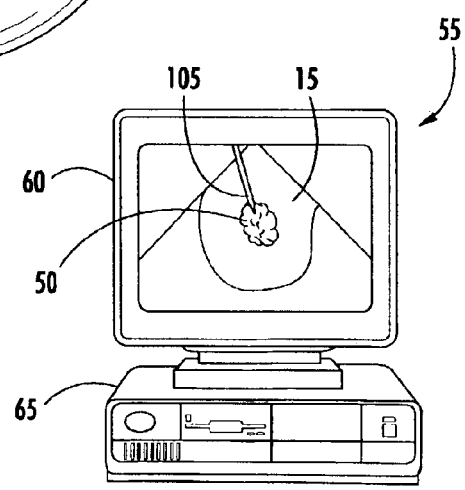
FIG. 2 is a perspective view of an ultrasound monitor displaying an echogenic needle that has been inserted into a uterus.

As illustrated in FIGS. 1 and 2, the ultrasound probe 100 is inserted into the uterus through the vagina. Once the probe is in place, the needle is inserted through the needle guide and into the uterus. The physician uses ultrasound imagery to locate the position of fibroids 50 and the needle 105 in the uterus. The tip of the needle 160 is directed against a targeted fibroid or its vascular supply and RF energy, cryogenic, or thermal treatment is applied to the fibroid to cause necrosis of the tissue. In this regard, FIG. 2 illustrates an ultrasound monitor 60 that is displaying ultrasound imaging of an echogenic needle 105 that has been inserted into a uterus 15. Normally, the probe sends data to an ultrasound unit 65 that processes the data and then displays the resulting images on the monitor.

Figure 3:
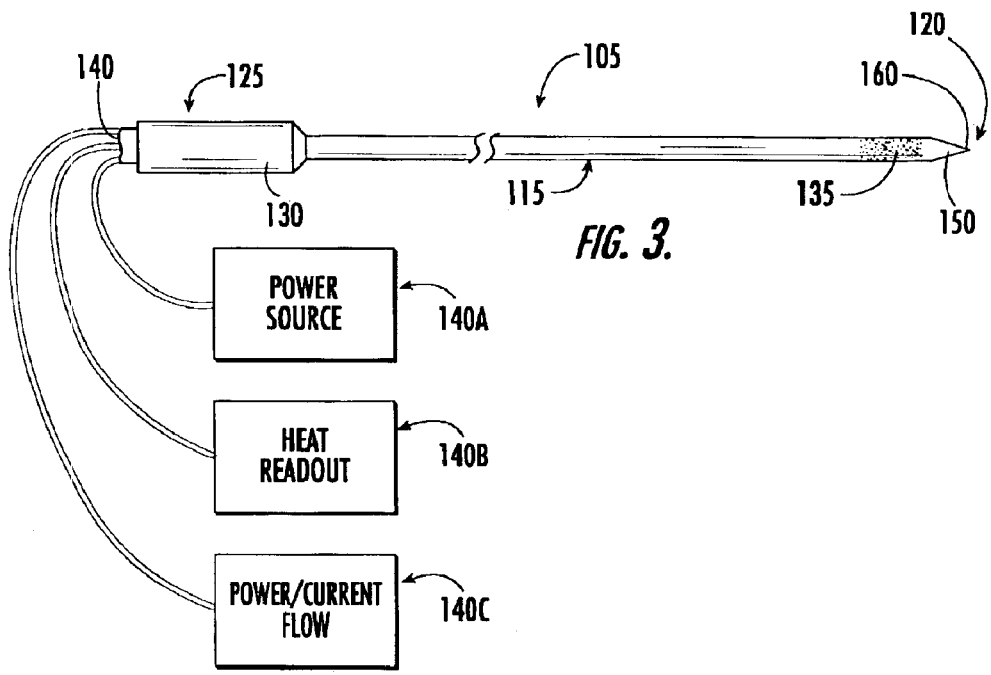
FIG. 3 is a side view of a radio frequency echogenic needle system for use with a transvaginal ultrasound probe.

In all embodiments, the needle will have an echogenic surface 135 at or near the distal end 120. For example, FIG. 3 shows a bumpy or uneven surface 135 on the outer member. Echogenicity refers to a surface's ability to reflect incident ultrasound waves back to a sensor. The more a surface reflects waves back to the sensor the greater its image will appear on an ultrasound display. Today, there is a variety of different techniques to increase a surface's echogenicity, including grooves or recesses, bumps, coatings, indentations, and the like. In the invention, the echogenic tip enhances its visualization and helps the physician to more precisely position the tip. Normally, the distal end of the needle or a segment proximal to the distal end will have an echogenic surface.

Inserting both the ultrasound probe and echogenic needle into the uterus through the vagina is very advantageous. Traditional laparoscopic myomectomy requires that the ablation needle be inserted into the uterus through the abdomen. During this procedure the needle must be inserted through the uterine serosa, which may result in the formation of uterine adhesions. In contrast, the invention provides an apparatus and method of use for fibroid myomectomy that is a minimally invasive surgical procedure. Adhesions are not expected to form with this method because the echogenic needle is inserted through the vagina rather than penetrating the uterine serosa. A second advantage of the invention is precision and accuracy. The echogenic needle has a heightened ultrasonic visibility that allows the physician to accurately locate and position the needle within the uterus. As a result, the surgical procedure is performed more quickly, the needle is easily repositionable by the surgeon, and most importantly the procedure will have a greater beneficial impact for the patient.

With reference to FIGS. 3 through 10, needles that are useful in the current invention are illustrated. The needle has an outer tubular member 115, a proximal end 125, a distal end 120, an insulation sheath 200 surrounding a portion of the outer member, and an echogenic surface 135 near the distal end.

As shown in FIG. 3, a RF needle is broadly designated by reference number 105. The needle 105 includes an active electrode at the distal end 120. Typically, the active electrode is a wire, wire loop, metal surface, or the like. The active electrode is in communication with an electrical connector 140 that is attached to the proximal end 125. The electrical connector 140 is connected to a RF power supply 140a so that RF current is supplied to the active electrode. The needle 105 is connected to a RF power source 140a, and optionally to a temperature display (heat readout) 140b.

Normally, the RF source will also include a means for controlling current to the active electrode. Typically, the RF needles will have a RF insulated sheath 200 that surrounds the outer member 115 and extends from the proximal end 125 to the distal end 120 leaving a segment of the outer member 120a (FIGS. 6 and 7) that is RF noninsulated. The RF insulation sheath may be made of any material that is suitable to prevent RF energy passing from the outer member to the tissue being treated, such as a heat shrink polyolefin or Teflon®.

The RF needle of the invention delivers either monopolar or bipolar current. With reference to FIGS. 4 through 9, a RF needle having a return electrode 210 is illustrated. The return electrode is connected to the power supply so that current passes through the active electrode into the fibroid tissue and back to the return electrode. Normally, the return electrode is located on the outer shaft 115 about 2 to 20 millimeters from the active electrode. Typically, the return electrode 210 is positioned in close proximity to the active electrode so that RF energy that passes from the active electrode through the fibroid is focused and does not dissipate within the uterus. Alternatively, as illustrated in FIG. 1, the return electrode 210a is located on an outer surface of the patient, such as the thigh or lower back. In this manner, current passes out of the active electrode 175 through the patient's tissue, and into the return electrode 210a.

Figure 4:
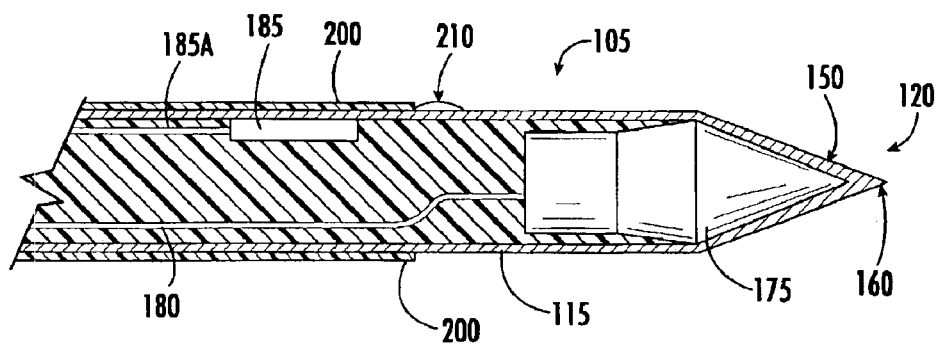
FIG. 4 is a sectional side view of the needle shown in FIG. 2.
Figure 5:
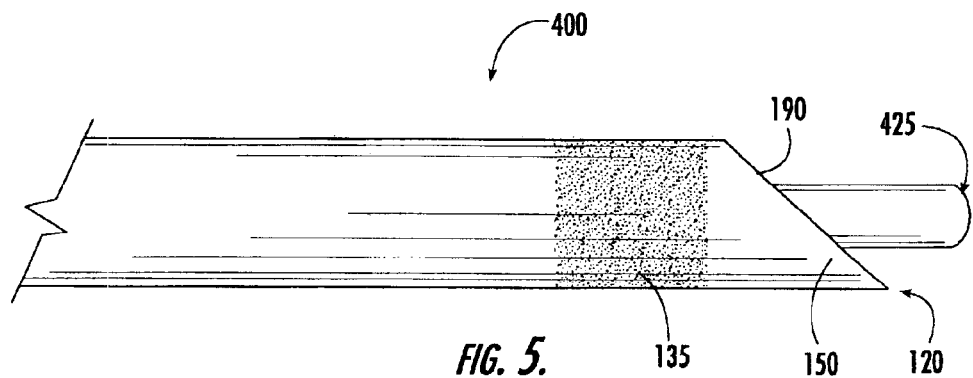
FIG. 5 is a sectional side view of a radio frequency echogenic needle having a "shut-off" mechanism.

In FIG. 4, the active electrode 175 is depicted at the distal end 120 within the needle. In this first embodiment, the distal end's noninsulated outer surface 150 is electrically conductive so that RF energy passes from the active electrode 175 into fibroid tissue. The distal end 120 has a sharpened tip 160 that can penetrate fibroid tissue to deliver RF energy within the fibroid. As shown in FIG. 4, the RF needle optionally has a temperature sensor 185 disposed near the distal end 120. Typically, the temperature sensor will be disposed near the tip of the needle or within the insulation sheath. Normally, the temperature sensor is a thermocouple or thermistor. The sensor provides information that enables the physician to monitor tissue temperature and to adjust the power accordingly.

With reference to FIGS. 5 through 9, reference number 400 broadly designates a RF needle having a RF energy "shut-off" mechanism. The shut-off mechanism turns off RF energy to the active electrode if the tip of the needle 190 penetrates through the uterine wall. Shutting off power to the active electrode serves several useful purposes. It prevents damage to healthy tissue, which would otherwise be coagulated by RF energy and it alerts the physician that the needle has punctured the uterine wall.

In contrast to the first embodiment, RF needle 400 has a sharpened beveled tip 190, an inner cylindrical member 405, and a spring 430 disposed within the outer member 115 at the outer member's proximal end 125. The inner member 405 is disposed and moveable longitudinally within the outer member 115. As illustrated in FIGS. 5 through 9, the inner member 405 has a forward end 407 and a blunt rear end 425. The forward end 407 is attached to the spring 430 that is connected to the needle's proximal end 125. In the at rest position, the blunt rear end 425 extends outwardly from the beveled tip 190 and is the first part of the distal end 120 to contact uterine tissue. Applying pressure to the blunt rear end 425 compresses the spring 430, and the inner member 405 slides longitudinally from the distal end 120 towards the proximal end 125. As a result, the blunt rear end 425 retracts into the outer member 115 and the beveled tip 190 contacts the surface of the targeted tissue.

In a first embodiment of RF needle 400, a segment of the inner cylindrical member has a cylindrical conductive surface, and outer member 115 has a second and third conductive surfaces on its inner surface. The second surface is in communication with the RF power supply 140, and the third surface is in communication with the active electrode 175. When in the rest position, the second and third surfaces are not in communication with each other. As pressure is applied to the blunt rear end 425 the inner member 405 retracts into a charged position. When in a charged position, the conductive surfaces 410, 415, and 420 are in communication and RF energy flows from the RF power source to the active electrode. If the distal end 120 punctures the uterine wall pressure against the blunt rear end 425 will be released and the spring 430 will rapidly extend the blunt rear end 425 outwardly. As a result, the conductive surface 410 will move longitudinally away from the second and third surfaces 415, 420 and RF energy supplied to the active electrode is shut-off. The exact position of conductive surfaces 410, 415, and 420 is not critical except that it is necessary that all three surfaces simultaneously communicate with each other when the inner member is in a retracted position.

Figure 6:
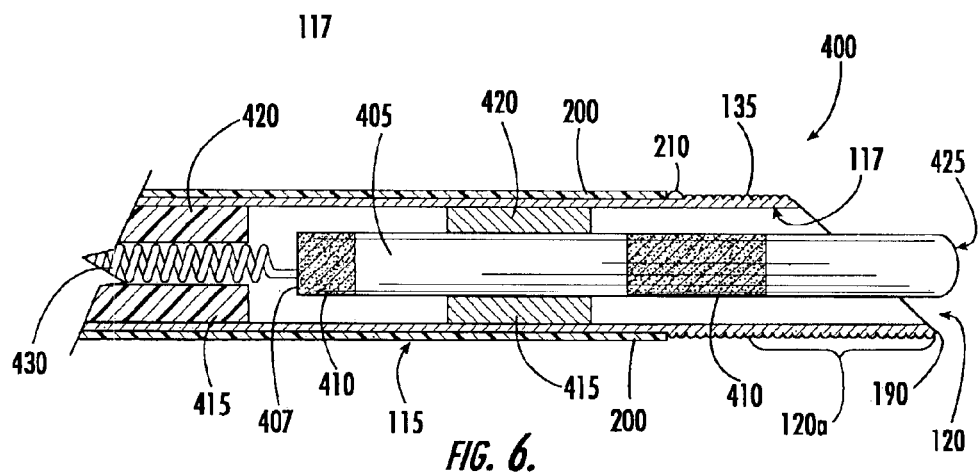
FIG. 6 is a sectional side view of a radio frequency echogenic needle having a "shut-off" mechanism and a noninsulated segment that is an active electrode.

In this regard, FIG. 6 shows a conductive surface 410 on the inner member 405. The conductive surface 410 is optionally located at the forward end 407 of the inner member 405 or at almost any position along the inner member. The second 420 and third surfaces 415 are located on an inner surface 117 of the outer member 115 so that when the inner member 405 retracts the conductive surfaces 410, 415, and 420 contact each other. When pressure is applied to the blunt rear end 425, the spring 430 compresses and the inner member retracts into the outer member 115. As a result, the conductive surfaces 410, 415, and 420 are in communication with one another and RF energy is delivered to the active electrode 175.

Figure 7:
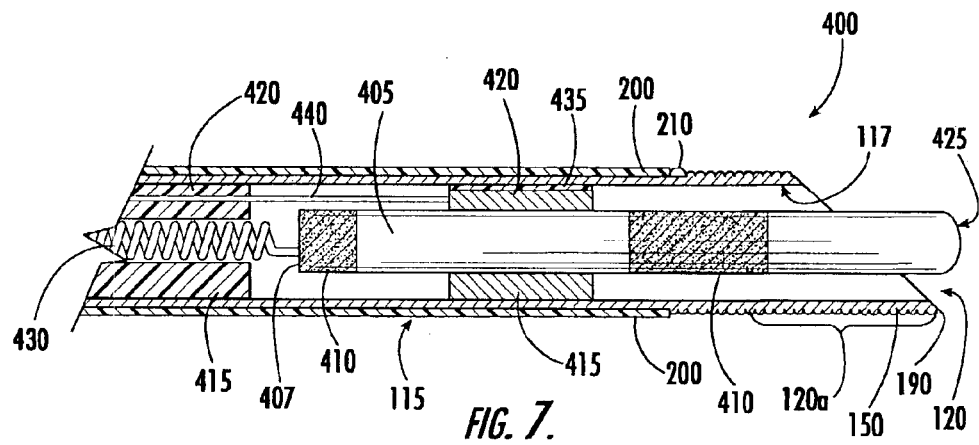
FIG. 7 is a sectional side view of a radio frequency echogenic needle having a "shut-off" mechanism and an active electrode disposed proximal to the distal end.
Figure 11:
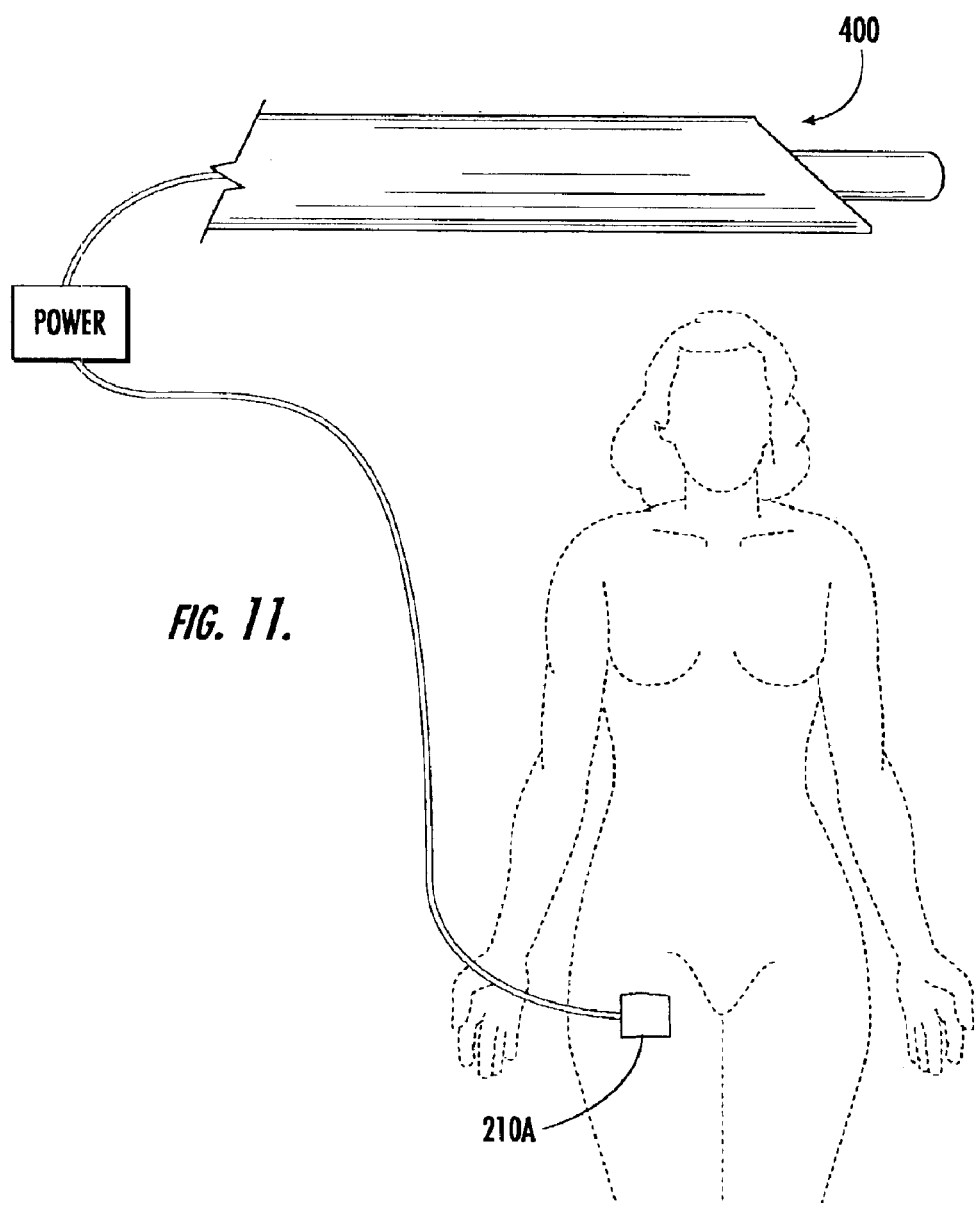
FIG. 11 is a side view of a radio frequency echogenic needle having a return electrode attached to a patient's thigh.

The active electrode is at the distal end 120 or alternatively, the noninsulated surface 120a of the outer member 115 is the active electrode. In this regard, FIG. 7 illustrates an RF needle having an insulation sheath 435 disposed between the second conductive surface 420 and the outer member 115. RF energy is supplied to the second surface through a current line 440 that is in communication with the electrical connector 140. As shown in FIG. 7, conductive surface 410 on the inner member 405 is in electrical communication with the outer member's 115 inner surface 117. Typically, the outer member is made from a material, such as stainless steel, that is electrically conductive and suitable for insertion into tissue. When the inner member 405 retracts into the outer member 115 the second surface 420 contacts the conductive surface 410 supplying RF energy to the noninsulated segment 120a. Optionally, insulation sheath 435 insulates the entire inner surface 117 of the outer member 115 except for segments at the active electrode 120a and the third conductive surface 415.

In a second embodiment of a needle having a safety mechanism 400, the active electrode is located at the blunt rear end. As shown in FIG. 8, the active electrode 175 is located at the blunt rear end 425 and an electrical connector 425a extends longitudinally from the conductive surface 410 to the active electrode 175. The outer member 115 has a second conductive surface 420 that is in communication with RF power supply, but rather than having a third surface in communication with the active electrode, the conductive surface 410 on the inner member 405 is in communication with the active electrode 175. When pressure is applied to the blunt rear end 425, the spring 430 compresses and the inner member retracts into the outer member. As a result, the conductive surfaces 410, 415 contact one another and RF current is applied to the active electrode 175. Typically, the electrical connector 425a is disposed within the inner member 405.

However, the electrical connector 425a may be disposed between the surface of the inner member and an optional RF insulation sheath that surrounds the inner member. The optional insulation sheath does not surround the conductive surface 410 or the active electrode 175.

In a third embodiment of a RF needle with a safety mechanism 400, the inner member is connected to a switch. With reference to FIG. 9, a needle is shown having an inner member 405 attached to a switch 450. The switch 450 is in communication with a RF power source via line 455. As pressure is applied to the blunt rear end 425 the inner member 405 retracts into the outer member 115 and closes the switch 450. When in the closed position, the switch 450 sends an electrical signal through line 455 to the RF power supply 140a and RF energy is delivered to the active electrode. The active electrode is located at the distal end and is in communication with the switch, or alternatively, the noninsulated distal end 120a is the active electrode.

In all the embodiments of a needle having a safety mechanism 400 the inner member 405 is typically made from a material that is non-conductive, such as a plastic. Normally, a non-conductive member will have a conductive material, such as stainless steel, inserted into a surface segment so that the inner member has an electrically conductive surface that will contact the second and third surfaces on the outer member. Somewhat more typically, the inner member is made from a metal such as stainless steel that is surrounded by a RF insulation sheath. The insulation sheath surrounds the inner member except for the conductive surface 410, which is RF non-insulated.

With reference to FIG. 10, a cryoablation needle is broadly illustrated by reference number 500. The cryoablation needle has an echogenic distal end having a sharpened tip 160. The outer member 115 is surrounded by a cryo-insulation sheath 200a. The insulation sheath 200a extends longitudinally from the proximal end 125 to the distal end 120 leaving a segment of the outer member 120a that is cryo-noninsulated. Normally, the sheath will be made of any material that prevents the cryogenic effect from passing through the outer member and into the surrounding tissue. A cryogen supply tube 510 is disposed within the outer member and extends from the proximal end 125 to the distal end 120. A cryogen supply source 520 provides cryogen supply through a cryogen connector 525 to the cryogen supply tube 510.

Typically, cryogenic liquids such as nitrogen, helium and argon are used to produce the cryogenic effect in the targeted tissue.

In all embodiments, it is necessary that the needle is longer than the ultrasound probe and has sufficient length to reach fibroids deep in the uterus. Typically, the length of the needle is about 25 to 50 centimeters, and somewhat more typically about 30 to 40 centimeters. The needle's diameter is dictated by the ultrasound probe's attached needle guide. Typically, the diameter of the needle is about 12 to 18 gauge, and somewhat more typically about 16 to 18 gauge. However, the needle is not limited to the above recited dimensions and may be varied depending upon the actual length of the probe and the needle guide's inner diameter. Typically, the outer member is made of any material that is suitable for insertion into tissue, such as stainless steel.

Optionally, as shown in FIG. 3, the needle will have a handle 130 at its proximal end 125. The handle 130 allows the user to easily manipulate and move the tip of the needle. Ideally, the handle 130 is large enough to be manipulated with the user's thumb, index finger and middle finger. Normally, the handle is metal, plastic, rubber, or the like.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An echogenic medical needle for transvaginal ultrasound directed reduction of uterine myomas and fibroids comprising:
    an electrically conductive outer tubular member having an inner surface, a distal end having a echogenic surface formed therein, and a proximal end;
    an active electrode near said distal end;
    a radiofrequency insulation sheath surrounding an outer portion of said outer member, said radiofrequency insulation defining a segment of said outer member that is insulated from radiofrequency and a segment of said outer member that is not radiofrequency-insulated, such that said radiofrequency insulation segment extends from said proximal end to said distal end;
    an electrical connector attached to said proximal end that is in electrical communication with said active electrode; and
    a vaginal ultrasonic probe baying an attached needle guide whereby said medical needle is positioned in said needle guide.

2. The medical needle according to claim 1, further comprising a radiofrequency power source in electrical communication with said electrical connector such that said power source provides electrical energy to said active electrode.

3. The medical needle according to claim 2, further comprising a safety device for shutting off said electrical energy to said active electrode comprising:
    an inner cylindrical member disposed within said outer member having a blunt rear end that extends outwardly from said open beveled tip, a forward end, and an electrically conductive outer surface that defines a portion of said inner member that is electrically conductive and a portion that is non-electrically conductive;
    a spring disposed within said outer member positioned at the proximal end of said outer member and attached to said forward end of said inner cylindrical member such that when pressure is applied to said blunt rear end said spring compresses and said blunt rear end retracts into said outer member;
    a second and third electrically conductive surface disposed on said inner surface, wherein said second and third surface are not in contact with each other, said second surface in electrical communication with said electrical connector, and said third surface in electrical communication with said active electrode, whereby retraction of said spring causes said first electrically conductive surface to simultaneously contact said second and third surface such that said electrical connector is in electrical communication with said active electrode.

4. The medical needle according to claim 3, wherein said second conductive surface is not in electrical communication with said inner surface.

5. The medical needle according to claim 2, further comprising a safety device for shutting off said electrical energy to said active electrode comprising:
    an inner cylindrical member disposed within said outer member having a blunt rear end that extends outwardly from said open beveled tip, a forward end, an active electrode disposed at said blunt rear end, and an electrically conductive outer surface that defines a portion of said inner member that is electrically conductive and a portion that is non-electrically conductive, said electrically conductive surface is in electrical communication with said active electrode;
    a spring disposed within said outer member positioned at the proximal end of said outer member and attached to said forward end of said inner cylindrical member such that when pressure is applied to said blunt rear end said spring compresses and said blunt rear end retracts into said outer member;
    a second electrically conductive surface disposed on said inner surface, wherein said second is in electrical communication with said electrical connector, whereby retraction of said spring causes said first electrically conductive surface to simultaneously contact said second surface such that said electrical connector is in electrical communication with said active electrode.

6. The medical needle according to claim 2, further comprising a switch to turn off maid electrical energy to said active electrode comprising:
    an inner cylindrical member disposed within said outer member having a forward end and a blunt rear end that extends outwardly from said open beveled tip, whereby applying pressure to said blunt rear end retracts said blunt rear end into said outer member;
    a switch that is disposed within said outer member having an open and closed position such that when said switch is closed said electrical connection and said active electrode are in electrical, communication, said switch connected to said forward end such that when said blunt rear end is retracted into said outer member, said forward end applies pressure to said switch whereby said switch is closed and said electrical connection and said active electrode are in electrical communication.

7. The medical needle according to claim 1, further comprising a return electrode disposed on said outer member proximate to said active electrode.

8. The medical needle according to claim 7, wherein said return electrode is disposed about 2 to 20 mm from said active electrode.

9. The medical needle according to claim 1, further comprising a return electrode disposed on an outer surface of a patient's body.

10. The medical needle according to claim 1, wherein said proximal end further comprises a finger grip for manually directing said distal end.

11. The medical needle according to claim 1, further comprising a temperature sensor that is disposed within said sheath near said active electrode, said sensor in communication with a temperature display means.

12. The medical needle according to claim 1, wherein said distal end further comprises a sharpened point for penetrating tissue.

13. The medical needle according to claim 1, wherein said attached needle guide is a plastic or metal clamp fitted around said probe having an opening through which the needle is inserted.

14. The medical needle according to claim 1, wherein said distal end further comprises an open beveled tip for penetrating tissue.

15. The medical needle according to claim 1, wherein the length of said outer member is about 25 to 50 centimeters.

16. The medical needle according to claim 1, wherein the length of said outer member is about 30 to 40 centimeters.

17. The medical needle according to claim 1, wherein the diameter of said outer member is about 12–18 gauge.

18. The medical needle according to claim 1, wherein the diameter of said outer member is about 16–18 gauge.

19. The medical needle according to claim 1, wherein said echogenic surface comprises grooves, recesses, bumps, indentations, or combinations thereof formed in the outer surface of said distal end.

20. A method for the electric surgery of myomas and fibroids in a uterus using a transvaginal ultrasound directed echogenic medical needle comprising the steps of:

a) providing an ultrasound probe having a transducer and a needle guide attached to said probe;

b) providing an echogenic needle, the echogenic needle including an electrically conductive outer tubular member having an inner surface, a distal end having a echogenic surface formed therein, a proximal end, an active electrode proximate to said distal end, a radiofrequency insulation sheath surrounding an outer portion of said outer member, said radiofrequency insulation defining a segment of said outer member that is insulated from radiofrequency and a segment of said outer member that is not radiofrequency-insulated, such that said radiofrequency insulation segment extends from said proximal end to said distal end and an electrical connector attached to said proximal end that is capable of being in electrical communication with said active electrode;

c) inserting said ultrasound probe into said uterus;

d) inserting said echogenic needle into said uterus through said needle guide;

l) sensing the location of said myomas and said echogenic needle within said uterus with imaging from said ultrasonic probe;

f) guiding said echogenic needle to a surface of said fibroid using said ultrasound imaging;

g) positioning said echogenic needle on said surface of said fibroid; and h) passing a controlled amount of radio frequency currant through said active electrode while said echogenic needle is in contact with said fibroid.

21. The method according to claim 20, wherein the stop of positioning the echogenic needle in contact with said myoma further includes the step of penetrating said surface with said distal and of said echogenic needle.

22. The method according to claim 21, wherein the step of providing an echogenic needle further includes the step of providing an echogenic needle as described in claims 11, 13, or 14.

23. The method according to claim 22, wherein the step of penetrating said surface further includes the step of shutting off power to said active electrode if said distal end pierces said uterus.

24. The method according to claim 20, wherein the step of positioning the echogenic needle in contact with said fibroid further includes the step of positioning said needle in contact with the fibroid's vascular supply.

25. The method according to claim 20, wherein the step of passing a controlled amount of radio frequency current through said active electrode while said echogenic needle is in contact with said fibroid further includes the step of monitoring the temperature changes in said fibroid.

26. The method according to claim 20, wherein said echogenic surface comprises grooves, recesses, bumps, indentations, or combinations thereof formed in the outer surface of said distal end.

* * * * *

UNITED STATES PATENT AND TRADEMARK OFFICE
CERTIFICATE OF CORRECTION

PATENT NO. : 6,936,048 B2  
DATED : August 30, 2005  
INVENTOR(S) : Hurst

It is certified that error appears in the above-identified patent and that said Letters Patent is hereby corrected as shown below:

Column 12,  
Line 13, "stop" should read -- step --.

Signed and Sealed this

First Day of November, 2005

JON W. DUDAS  
*Director of the United States Patent and Trademark Office*